(12) United States Patent
Galeote (10) Patent No.: US 7,843,192 B2
(45) Date of Patent: Nov. 30, 2010

(54) KIT, METHOD AND APPARATUS FOR MONITORING OPERATION OF A BEARING ASSEMBLY, METHOD FOR PRODUCING SAID APPARATUS, AND BEARING ASSEMBLY WITH A CONDITION MONITOR

(75) Inventor: Brian Galeote, Kanata (CA)

(73) Assignee: National Research Council of Canada, Ottawa, ON ( * ) Notice: Subject to any disclaimer, the term of this patent is extended or adjusted under 35 U.S.C. 154(b) by 596 days.

(21) Appl. No.: 11/889,811

(22) Filed: Aug. 16, 2007

(65) Prior Publication Data
US 2009/0046964 A1    Feb. 19, 2009

(51) Int. Cl.
*G01R 33/12* (2006.01)
*G01N 27/72* (2006.01)

(52) U.S. Cl. ........................ 324/234; 324/238; 324/240

(58) Field of Classification Search .................. None
See application file for complete search history.

(56) References Cited

U.S. PATENT DOCUMENTS

| | | | |
|---|---|---|---|
| 4,169,629 A | | 4/1980 | Phillips |
| 4,259,637 A | * | 3/1981 | Bloomfield et al. ......... 324/166 |
| 4,864,239 A | * | 9/1989 | Casarcia et al. ............. 324/262 |
| 5,509,310 A | * | 4/1996 | El-Ibiary ..................... 73/660 |
| 5,677,488 A | | 10/1997 | Monahan et al. |
| 5,854,553 A | * | 12/1998 | Barclay et al. ......... 324/207.16 |
| 6,484,582 B2 | | 11/2002 | Ehrfeld et al. |
| 6,571,632 B1 | | 6/2003 | Browner et al. |
| 6,741,073 B2 | * | 5/2004 | Iwamoto et al. ............. 324/174 |
| 6,802,221 B2 | | 10/2004 | Hedeen et al. |
| 6,803,757 B2 | * | 10/2004 | Slates ..................... 324/207.17 |
| 7,107,168 B2 | * | 9/2006 | Oystol et al. .................. 702/94 |
| 2002/0145120 A1 | * | 10/2002 | Adams et al. .......... 250/559.29 |

FOREIGN PATENT DOCUMENTS

WO    WO 2006/083736    8/2006

OTHER PUBLICATIONS

Abstract of Japanese Publication No. 59097316, Jun. 5, 1984, Toshiba Corp.
Yu, John J. et al., "Detection of Rolling Element Bearing Defects" Proceedings of ASME FEDSM'01, FEDSM2001-18089, May 29-Jun. 1, 2001, pp. 375-384.
Young, M.C.S. et al., "DSP Applications in the Condition Monitoring of Bearings" DSP in Instrumentation, IEE Colloquium on (Digest No. 009) (1992) pp. 3/1-3/4.
Eddy Current Monitoring System (ECMS). Techincal specification 7.02/1.0S. Rothe Erde GmbH. (2006).

* cited by examiner

*Primary Examiner*—Jay M Patidar
(74) *Attorney, Agent, or Firm*—Jason E. J. Davis

(57) ABSTRACT

A technique for determining properties of a bearing assembly in use involves using an eddy current probe for detecting changes in material density within a raceway of the bearing assembly. A field of detection of the eddy current probe enters the bearing raceway intermediate races that define the raceway, and as such the detection is of the bearing elements, and not deflections in a wall that defines the raceway.

20 Claims, 10 Drawing Sheets

KIT, METHOD AND APPARATUS FOR MONITORING OPERATION OF A BEARING ASSEMBLY, METHOD FOR PRODUCING SAID APPARATUS, AND BEARING ASSEMBLY WITH A CONDITION MONITOR

FIELD OF THE INVENTION

The invention relates in general to a method of monitoring bearing assemblies, and, in particular, to the accurate, non-invasive monitoring of bearing assemblies in use.

BACKGROUND OF THE INVENTION

Bearing assemblies used in a majority of low-friction rotational couplings are subject to wear, and can be damaged by use when worn. Typically bearing assemblies are defined by a raceway between two opposing races, in which bearing elements are retained. It is also common to have a cage which constrains the bearing elements to motion within a range to ensure a distribution of the bearing elements within the raceway, resulting in a balanced distribution of stresses imparted on the bearing assembly.

Skidding, the gross sliding of a bearing element bearing surface relative to one of the races is a principal indicator (and cause) of wear. Skidding is generally a high-speed phenomenon caused by a difference between inner and outer race-bearing element loading (mainly caused by the centrifugal force of the bearing element). Increasing applied load to the bearing can decrease skidding, but will tend to reduce fatigue endurance. So a compromise between the degree of skidding allowed and bearing endurance must generally be accepted, and lubrication regimes are chosen with the degree of skidding in mind.

Skidding results in surface shear stresses of significant magnitudes. If a lubricant film generated by the relative motion of the bearing element within the raceway is insufficient to completely separate the surfaces, surface damage known as "smearing" will occur. Smearing is a severe type of wear characterized by metal tightly bonded to a race and/or the bearing element caused by transference. Smearing causes roughness in the contact areas which is detrimental to any bearing assembly. An amount of skidding is to be controlled in any application since at the very least it results in increased friction and heat generation even if smearing does not occur.

Skidding is a particular problem in cylindrical bearing element bearings used to support shafts in high speed and/or high load applications. These bearings, which are used principally for localization of spinning parts, are very lightly loaded while operating at high speeds making them very susceptible to skidding.

In some applications high radial stresses are applied to bearing assemblies, especially when the bearing assemblies support shafts that rotate at high rates. In some applications nominal stresses are applied, but vibrations, imbalance of the bearing assembly, or failure caused by worn or otherwise damaged bearing assemblies, can result in catastrophic failure of critical systems. While backup systems and other fail-safe measures are built into may critical systems, the use of bearing assemblies still requires preventative maintenance programs. Typically, to reduce a likelihood of failure, bearing elements are replaced after a number of operating hours according to a Diagnostic, Prognostic and Health Management program, or the like. The reliance on a number of operating hours is not an ideal solution because of a high cost of precision bearings and the shortening of their duty life, costs of down time of the equipment, possible absence of a backup for a critical system while one system is taken off-line or costs of multiple backup systems to ensure that there is a backup, etc. Consequently, in choosing the number of operating hours (or corresponding measure of amount of use) before replacement, a trade off is made between reducing a probability that the bearing will undergo a failure, and the costs of replacing the bearing.

A need for in situ sensors has therefore been acknowledged, and a number of these systems have been developed. A majority of bearing monitoring systems known in the art appear to use vibration sensing equipment to detect the onset of failure.

While vibration sensing equipment may provide adequate notice for some applications, in others the bearing assembly has suffered irreversible damage by the time the failure of the system is detected. Once vibrations are manifest, the damage sustained may extend beyond the bearing elements to the cage, and to the opposing races necessitating replacement of larger pieces. Furthermore, with vibration analysis, it may be difficult to detect failures and problematic operation for equipment in large, interconnected, complex machinery, as identification of which parts caused which vibration may be difficult.

Further still applicant has found that vibration analysis does not work on turbines of jet engines, for example. These high-efficiency rotational couplers are very quiet, and consequently, even in isolation, vibration analysis does not provide desirable information.

In particular, as is well known in the art, skidding of bearing elements within bearing assemblies is of particular interest for determining how long a bearing assembly should be used in the given mode of operation. To this end, it is highly desirable to be able to compute a ball pass frequency to determine a rate of revolution of the bearing elements within the raceway.

It has recently been suggested to provide sensors within bearing assemblies, either within bearing elements themselves, or within the cage. For example, it has been suggested to provide sensors (i.e. eddy current displacement gauges) within a center of a cylindrical ball bearing, as taught by Kazao et al. in Japanese Patent Abstract application number 57204590 (publication number 59097316 A).

PCT application WO 2006/083736 to Varonis teaches an antifriction bearing having a sensing unit for sensing a condition of the bearing, wherein the outer race has a power transmitting coil and a receiver and the cage has a power receiving coil and a transmitter for sending a signal of the sensed condition of the bearing to the receiver in the outer race.

While there may be applications for which these systems are suited, Applicant has found that small variations in mass to a cage causes an imbalance of the whole bearing assembly that is unacceptable for bearing assemblies that operate at high revolution rates. For example, an experiment where small notches were removed in a cage for a bearing assembly for radial load designed to operate up to 35,000 rpm failed at about 20,000 rpm in one experiment. Accordingly in some applications (including most all high speed applications), cage mounted sensors could not be implemented without some very accurate weight distribution control that may not be feasible or desired at a given cost point, if at all possible.

Furthermore the expense of multiple receiving and transmitting coils embedded in the cage and an outer race, according to the teachings of Varonis, and equipment for communicating the signal to a processor increase costs of parts and engineering design requirements of the overall system.

Other systems have been designed that detect vibration directly at an outer race surface to monitor and analyze bearing conditions. Strain gages were initially used by Shapiro of the Franklin Institute. Later the strain gages were replaced by non-contact fiber optic techniques by Philips et al. of the Naval Research and Development Center (U.S. Pat. No. 4,196,629). Bentley Nevada of Minden Nevada has published on the Internet, a paper outlining a system for monitoring and analyzing bearing conditions that summarizes the above evolution and replaces the fiber optic techniques with an eddy current proximity transducer.

In these systems, detection equipment is arranged on a wall of the bearing assembly, abutting a piece providing the outer race, which is consequently a bearing wall. If the piece is too thick, or irregularly shaped, it can be difficult to correctly associate deflections with events within the bearing assembly. However, it is common practice to provide replaceable bearing assemblies which have relatively thin radial walls that transmit these deflections, and mechanical deflections are most noticeable at this location. A probe according to the system described by Bentley Nevada is directed radially from an axis of rotation of the bearing assembly on the radial, bearing wall. Thus the eddy current probe is aligned with the principle stresses borne by the bearing assembly.

Unfortunately, equipment in use provides a housing surrounding the radial wall of bearing assemblies, and this housing is important for providing uniform structural support for the bearing assembly. To provide a probe with access to the piece providing the outer race through the attendant equipment, an opening is needed in the housing. It is, however, not desirable to provide an opening in the housing as this presents a structural weakness in the housing. Such a structural weakness may actually decrease a service life of the bearing assembly. Accordingly knowledge of properties of the bearing assembly tested in a modified housing may not be an accurate predictor of the bearing assembly in use in equipment with the unmodified housing. Furthermore, it is not generally possible to test equipment in situ with this method, unless the housing is altered to provide a structural weakness, or a modified housing is provided. A time needed for replacing the housing with an altered housing for in situ testing and returning the housing for continued normal use may make this method less attractive. Furthermore, any inaccuracy of the results of testing of a bearing assembly, or any imperfections in the bearing assembly caused by operation within the altered housing may be of concern.

There therefore remains a need in the art for a technique for monitoring a bearing assembly.

SUMMARY OF THE INVENTION

The invention provides a solution to the above identified problem that involves placing an eddy current probe to face a non-bearing surface of the bearing assembly. While this does not permit the detections of deflections as bearings pass by a bearing wall supporting a race of the bearing assembly, Applicant has found that if the probe is adapted for detecting a change in density, the density of the ball bearing passing across the race provides useful information regarding the operation of the bearing assembly, and can be used to determine, for example, a ball pass frequency measure, which can be used to determine an amount of skidding bearing elements undergo in operation.

This configuration obviates the problems with accessing a structural wall of the bearing assembly, and alters the mechanism for detection. While in the system according to Bentley Nevada measures deflections in the radial, bearing, wall, the Applicant has found that detection of the density changes as the bearing elements pass by provides information sufficient to determine relevant features of the operation of the bearing assembly.

Accordingly, an apparatus is provided for monitoring operation of a bearing assembly. The apparatus includes: an eddy current probe for detecting a change in material density within a volume in front of a tip of the probe, and a fixture for mounting the probe in a stable position with the tip of the probe proximate a raceway of the bearing assembly so that part of the volume enters the raceway at a position intermediate opposing races that provide supporting walls of the raceway. Accordingly the probe is not directed substantially through either supporting wall. For example, the fixture may be mounted on or adjacent a relatively stationary part of the bearing assembly.

If the bearing assembly is for bearing a principally radial load, the probe is positioned with its tip substantially intermediate the inner and outer race above or below the raceway, the probe being directed at least partially in a direction of an axis of rotation of the bearing assembly. Preferably the probe is directed mostly in the direction of the axis, and in some embodiments the probe is substantially parallel to the axis.

If the bearing assembly is for bearing a principally axial load, and the probe is positioned with its tip intermediate the inner and outer race, the probe being directed at least partially in a direction radially inwardly or outwardly of the bearing assembly. Preferably the probe is directed mostly in the radially inwardly or outwardly direction, and in some embodiments the probe is substantially perpendicular to the axis.

Accordingly a bearing assembly with a condition monitor is further provided. The bearing assembly includes a rotating part having a meeting surface defining a first race, a supporting part having a complementary surface defining a second race, and a plurality of bearing elements, the rotating and supporting parts arranged so that the first and second races are facing each other to define a closed raceway for the bearing elements. The bearing assembly further including an eddy current probe for detecting a change in material density within a volume in front of a tip of the probe, and a fixture for holding the probe in a stable, operative position with respect to one of the supporting part and the rotating part of the bearing assembly so that the tip of the probe is directed with at least part of the volume enters the raceway at a position intermediate the first and second races, whereby the probe is not directed substantially through either of the supporting walls.

The fixture may be mounted on or adjacent the stationary part of the bearing assembly.

If the bearing assembly is for bearing a principally radial load, the probe is positioned with its tip substantially intermediate the inner and outer race axially above or below the raceway, the probe being directed at least partially in a direction of an axis of rotation of the bearing assembly. Preferably the probe is directed mostly in the direction of the axis, and in some embodiments the probe is substantially parallel to the axis.

If the bearing assembly is for bearing a principally axial load, and the probe is positioned with its tip intermediate the inner and outer race, the probe being directed at least partially in a direction radially inwardly or outwardly of the bearing assembly. Preferably the probe is directed mostly in the radially inwardly or outwardly direction, and in some embodiments the probe is substantially perpendicular to the axis.

Also accordingly, a method for producing an apparatus for monitoring operation of a bearing assembly is provided. The method involves providing an eddy current probe for detecting a change in material density within a volume in front of a tip of the probe, and retaining the probe in a stable position relative to a stationary part of the bearing assembly to position the tip of the probe with at least part of the volume entering a raceway of the bearing assembly at a position intermediate inner and outer races that provide supporting walls of the raceway, whereby the probe is not directed substantially through either supporting walls. Supplying power to the probe and driving the bearing assembly permits detection of bearing elements circuiting the raceway.

A method for monitoring operation of a bearing assembly in use is also provided. The method for monitoring involves: providing an eddy current probe for detecting a change in material density within a spatial region in front of a tip of the probe, retaining the probe in a stable position relative to a stationary part of the bearing assembly to position the tip of the probe with at least part of the spatial region passing into a raceway of the bearing assembly from a position intermediate inner and outer races of the raceway that provide supporting walls of the raceway, whereby the probe is not directed substantially through either supporting wall. The method of monitoring further comprises supplying power to the probe from a power supply to activate the probe to detect changes in material density within the raceway at a given sample rate while the bearing assembly is in operation, and capturing data from the probe in a stream of data at a sample rate greater than a cycling rate of a cage of the bearing assembly. The method of monitoring further comprises analyzing the captured data to determine properties of the bearing assembly in use.

Analyzing may involve determining ball pass frequency of the bearing assembly.

A kit for monitoring operation of a bearing assembly is also provided. The kit includes an eddy current probe for detecting a change in material density within a volume in front of a tip of the probe instructions for effecting the method of monitoring. The kit may further include program instructions for carrying out an analysis of data captured from the eddy current probe to determine properties of the bearing assembly in use.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

The invention provides for the monitoring of a bearing assembly in operation, and does not require modification or removal of a housing supporting the races in the principal bearing direction of the bearing assembly.

The invention can be applied in a number of contexts. It can be applied within a laboratory setting, in a controlled setting, or in a machine in use. The bearing assembly may be tested in isolation, as a part of a machine, or as a whole machine. The test may be part of a diagnostic or prognostic investigation on a part of a machine, it may be part of routine maintenance, or it may be a continuous or intermittent sensing process. The testing may be on a new bearing assembly in operation, for example for product verification, or for verifying interworking with other parts of a machine, or may be performed on a bearing assembly of a device in use, or may be performed on a bearing assembly suspected of approaching an end of its service life. Further the invention may be applied to determine a Diagnostic Prognostic and Health Management Program for the bearing assembly, or to otherwise test the machine, for example in harsh environmental conditions, in irregular use scenarios, etc.

Figure 1A:
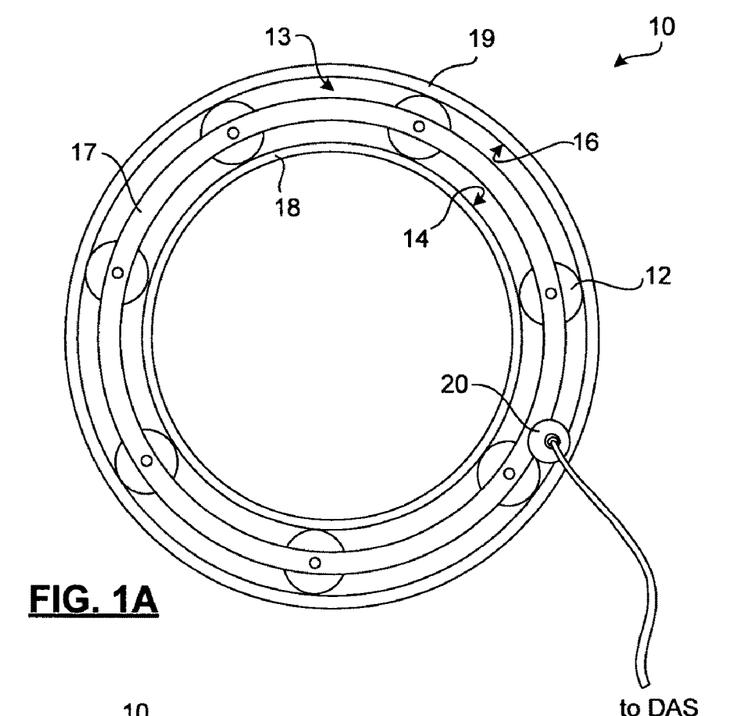
FIGS. 1a,b are two views of a schematic illustration of a radial-load bearing assembly equipped with an eddy current probe in accordance with an embodiment of the invention.
Figure 1B:
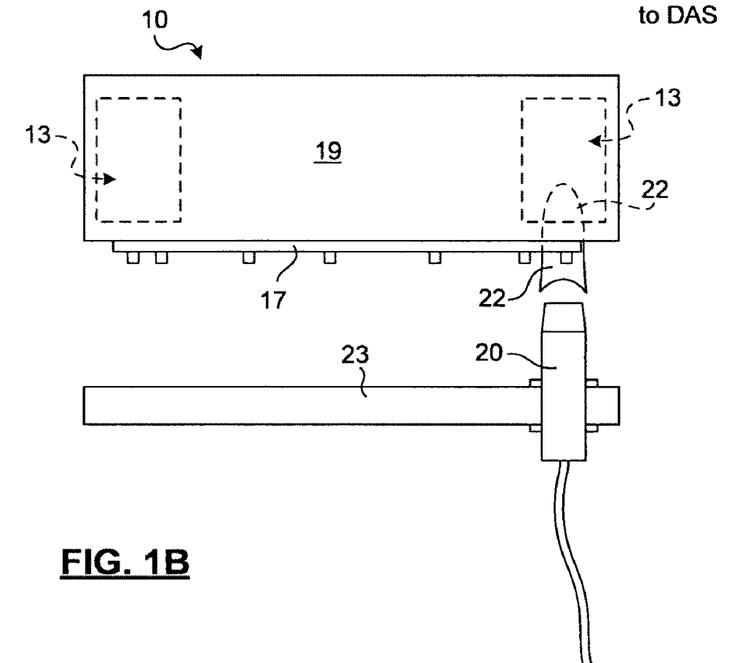

FIGS. 1A,B are schematic illustrations of a configuration of a bearing assembly 10 for monitoring in accordance with an embodiment of the invention using a proximity detector. The bearing assembly 10 illustrated is an independently replaceable unit designed to take a radial load. The bearing assembly 10 has a plurality of bearing elements 12 constrained to move in a closed circular raceway 13 that is defined at opposite sides by an inner race 14, and an outer race 16. The inner race 14 is a bearing surface that faces radially outwardly, and the outer race 16 is a bearing surface facing radially inwardly. A cage 17 is provided to maintain spacing of the bearing elements 12 within the raceway 13. Conventional bearing assemblies of the kind shown in FIG. 1 provide a (relatively) stationary part and a rotating part. While, more often the outer raceway is provided on the stationary part, and the inner raceway is provided on the rotating part, which is adapted for coupling to a shaft, this is inverted in some machines. The inner 14 and outer 16 races are formed to provide a desired clearance of the bearing elements 12, and are strong enough to support the rated load distributed over the contact points of the bearing elements 12, which is a small surface area. This pressure is borne by inner 18 and outer 19 walls.

Herein a rate of revolution of the bearing assembly refers to a rate of revolution/cycling rate of the rotating part of the bearing assembly with respect to the (relatively) stationary part. A cage rate is a rate of revolution/cycling rate of the cage with respect to the stationary part. A ball pass frequency is the number of ball passes per unit time from any fixed point on the stationary part of the bearing assembly. Accordingly, in a principally radial load bearing assembly, a BPFO measurement is the ball pass frequency measured from the outer race, the ball pass frequency measured from the inner race corresponds to a BPFI measurement.

While the inner and outer walls 18, 19 are relatively thin in the illustrated embodiment, this is because it is generally desirable for the bearing assembly 10 to be independently removable and replaceable. Accordingly it will be appreciated that before significant loads are applied to such a bearing assembly 10, the assembly 10 will be installed in a housing (not shown). The housings used vary considerably depending on the machine being used.

As will be noted by those of skill in the art, bearings 12 come in different shapes, and can generally be separated into two classes: ball bearings, and roller bearings. Ball bearings are ball-shaped and are free to rotate in any direction, in use. Roller bearings generally provide one (conic) or two (cylindrical, frustoconical, barrel, etc.) axial surfaces and a bearing surface along which the bearing element rolls. Spherical roller bearings are also know that do not have distinct axial surfaces but are intended in use to roll along an established axis, FIG. 1 shows 7 cylindrical bearings, and accordingly the races 14, 16 are cylindrical walls having linear profiles in the illustrated embodiment, but it will be appreciated by those of skill in the art that other bearing element types could be used in the practice of this invention, including barrel shaped, and, where an angle between the axis of rotation of the bearing assembly and the (principal) axis of rotation of the bearings is neither parallel nor orthogonal, a conical or frustoconical bearing can be used. Corresponding races of various configurations are known in the art.

While the illustrated bearing assembly 10 is a replaceable unit, in other embodiments the outer race could be machined directly into a supporting piece, and/or the inner race could be machined onto a shaft, for example. In either case the invention provides access to the bearing assembly from a direction that is substantially orthogonal to the direction(s) of principal load of the bearing assembly. Accordingly, there is no weakening of the housing in the crucial direction required to place the probe.

The proximity detector used for this patent operates on an eddy current principle. Current flows through a coil at the tip of an eddy current probe 20 producing a magnetic field. The magnetic field emitted by the probe 20 is a function of the distance from the probe tip and a material density in the neighbourhood of the tip. The magnetic field produced by the probe 20 can penetrate a dense piece inducing a magnetic field within the piece. The induced magnetic field varies with a nature and density of material in the space and its distance resulting in a change in the resistance (impedance) of the coil within the probe. These resistance changes are typically converted into a voltage modulated signal output by the probe. The voltage output may be measured by a data acquisition system (DAS).

The eddy current probe 20 is provided for monitoring the operation of the bearing assembly 10. The eddy current probe 20 is positioned near the cage area of the bearing assembly, and is held in place by any convenient means. In particular the tip of the eddy current probe 20 may be positioned adjacent to the raceway intermediate the inner and outer races. For example, a cover plate 23 of the bearing element bearing assembly may be modified to support the probe, as shown in FIG. 1b.

The probe 20 is calibrated to detect a change in density in a spatial region 22 extending in front of a tip of the probe 20. It will be appreciated by those skilled in the art that the spatial region 22 is schematically shown and is a graduated field with no discrete boundaries. Furthermore the field of interaction of the probe 20 varies with the substances and configurations of material in the field. The probe 20 is directed orthogonally to the direction of the principal stresses borne by the bearing assembly 10, which is, in this case, a direction substantially parallel to the axis of the bearing assembly.

While it may be preferable to align the probe tip normal to a plane of the raceway 13 as shown, so that the spatial region 22 penetrates maximally into the raceway 13, it will be appreciated that this is not necessary, and may not be preferable in some situations. For example, where a clearance is not sufficient to house a desired probe, the probe may be directed at an angle. It will be appreciated that for a given probe 20 and a given separation of the probe from the cage 17, a depth of the overlap of the spatial region 22 and the raceway 13 depends on a sine of a minimal angle between the axis of the probe 20 and the plane of the raceway 13, and therefore an ability of the probe 20 to detect positions of the bearing elements is dependent on the depth of the probe's spatial region 22, a separation of the probe 20 from the raceway 13, and the angle. Accordingly it may be preferable that the probe is directed more axially than radially or azimuthally The probe 20 has a power supply cable attached to a power supply, and an output coupled to a data acquisition device, such as a general purpose computer. As is well known in the art, an eddy current probe coil typically outputs a resistance modulated signal representative of a distance of a metal part from the probe tip, according to a configuration and calibration scheme associated with the eddy current probe. Commercially available the eddy current probes usually come with analog circuitry for converting the resistance changes into a voltage modulated output, improving a quality of the signal, and for correcting for any non-linearities/imperfections in the eddy current probe. In accordance with the present invention the absolute value of the output values, and how they relate to distances is not of interest. Rather, given the cyclic nature of the apparatus, detection of a pattern of changes in the output values is sufficient to identify the passings of the bearing elements 12, as is further discussed below with reference to FIG. 3.

The analog circuitry may serve as an interface between the probe and a data acquisition processor. Typically the analog circuitry supplies voltage to the probe and senses any impedance changes in the probe, and outputs the detected changes. Typically output voltages of 0 to 24 volts are preferred for signal analysis cards, corresponding to proximity changes of around 200 millivolts per mil (thousandth of an inch).

It will be appreciated that the functional core of this apparatus is a probe (usually a many-winding coil) that is energized by an electrical signal, for which a resistance change can be detected and outputted for signal analysis, the probe being mounted and directed towards the raceway through a space between the opposing races, as opposed to completely through one of the races.

This apparatus may be realized in a number of different embodiments, including those using a wireless communications device for transmitting a signal representing information for monitoring the bearing assembly detected by the probe. The communications device may conditionally or unconditionally transmit the signal (e.g. in dependence upon a time or operating condition of a machine of which the bearing assembly is a part, or upon demand from a processor or user, or depending on a change in the signal for example: compared to a baseline, a previously established pattern, or a previous signal segment, and/or in dependence upon an output from an analyzer or artificial intelligence program that analyzes the signal to determine warnings), may store data, and may pre-analyze data (for example it is known to apply signal transformations to compensate for non-linearity/defects of the probe used, to smooth the signal, etc), perform data analysis and may apply an artificial intelligence program to this end. A probe may be connected to an RF-Id tag or the like for the communications. The RF-Id tag could be used to charge the probe, temporarily store measurement data output by the probe, and exchange the data with an RF-Id tag reader, in a manner known in the art. Applicant prefers using a probe with an independent power supply in the examples in order to provide a power in the range of 0.8 W, but the high quality of the signals produced indicate that a lower power can be used and still provide useful information such as a BPFO. The probe 20 may also be connected to a maintenance and monitoring system for monitoring a number of sensors in the machine that it is serving.

Figure 2A:
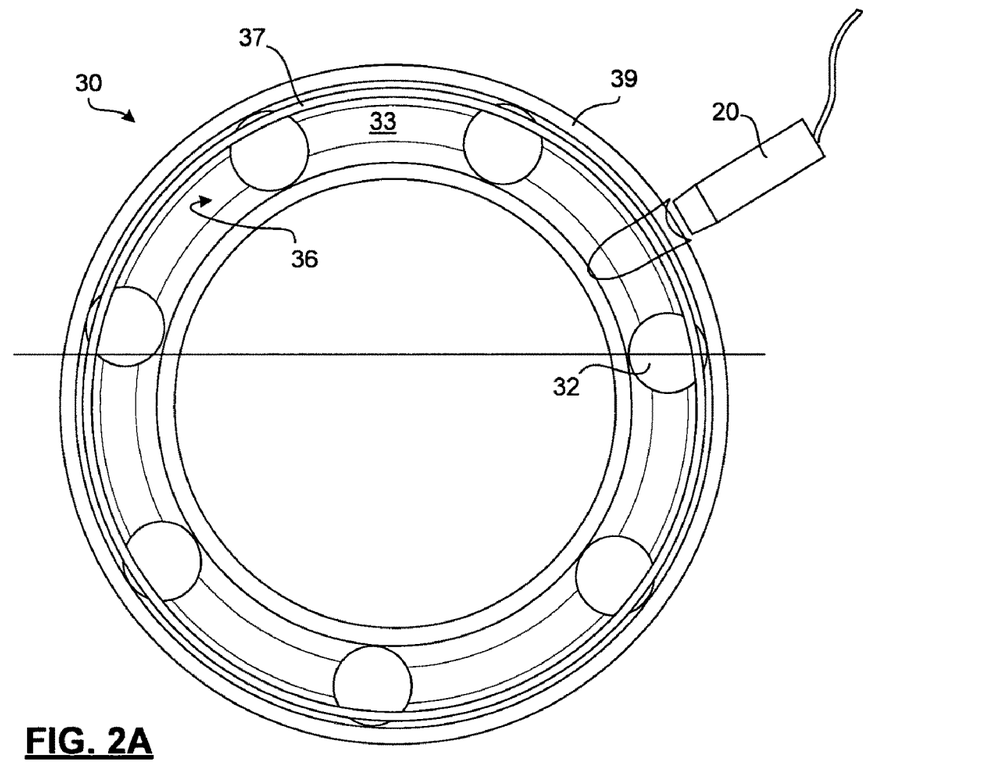
FIGS. 2a,b are two views of a schematic illustration of an axial-load bearing assembly equipped with an eddy current probe in accordance with an embodiment of the invention.
Figure 2B:
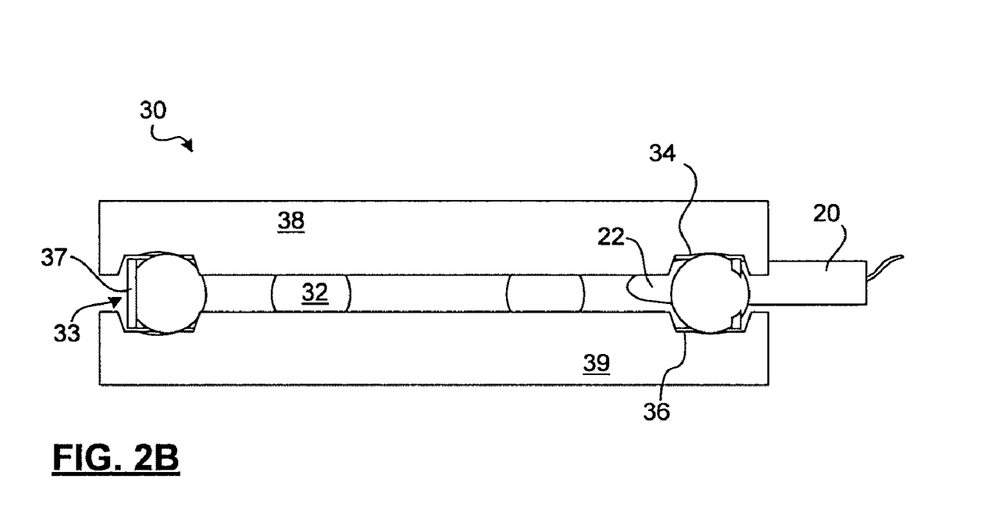

FIGS. 2*a,b* schematically illustrate a configuration of a second bearing assembly 30 at which the present invention may be deployed. FIG. 2*a* shows the bearing assembly 30 with a top part 38 that defines an upper race 34, removed to show the pieces. FIG. 2*b* shows a second view of the same bearing assembly 30 with the top part 38 included, viewed in cross-section along the plane AA shown in FIG. 2*a*. The bearing assembly 30 consists of parts 32-39 that are analogous to parts 12-19 of bearing assembly 10, respectively, and listing of these parts is not repeated herein except to indicate differences between the two.

Bearing assembly 30 is adapted to bear a principally axial load, and accordingly the top and bottom opposing races 38, 39 face parallel to the axis from opposite directions. Unlike the cylindrical bearing element, a spherical bearing element can bear some off-axis forces, as the races do not have linear profiles. Accordingly, the top and bottom opposing races 38, 39 have a bearing part that has a semicircular profile for bearing the off-axis loads.

The principal stresses borne by the bearing assembly 30 are axial, and accordingly housings for encasing the bearing assembly 30 from above and below (in the axial direction) may be used to support the bearing assembly 30. The probe 20 for monitoring the bearing assembly 30 is consequently directed radially, and may be radially inwardly as shown, so that probe leads can more easily exit a machine and/or housing in which the bearing assembly 30 is situated. As with the previous embodiment, the probe does not need to be directed radially, but could be directed at an angle. Preferably the probe is directed mostly in the radial direction to maximize penetration of the spatial region into the raceway.

Figure 3:
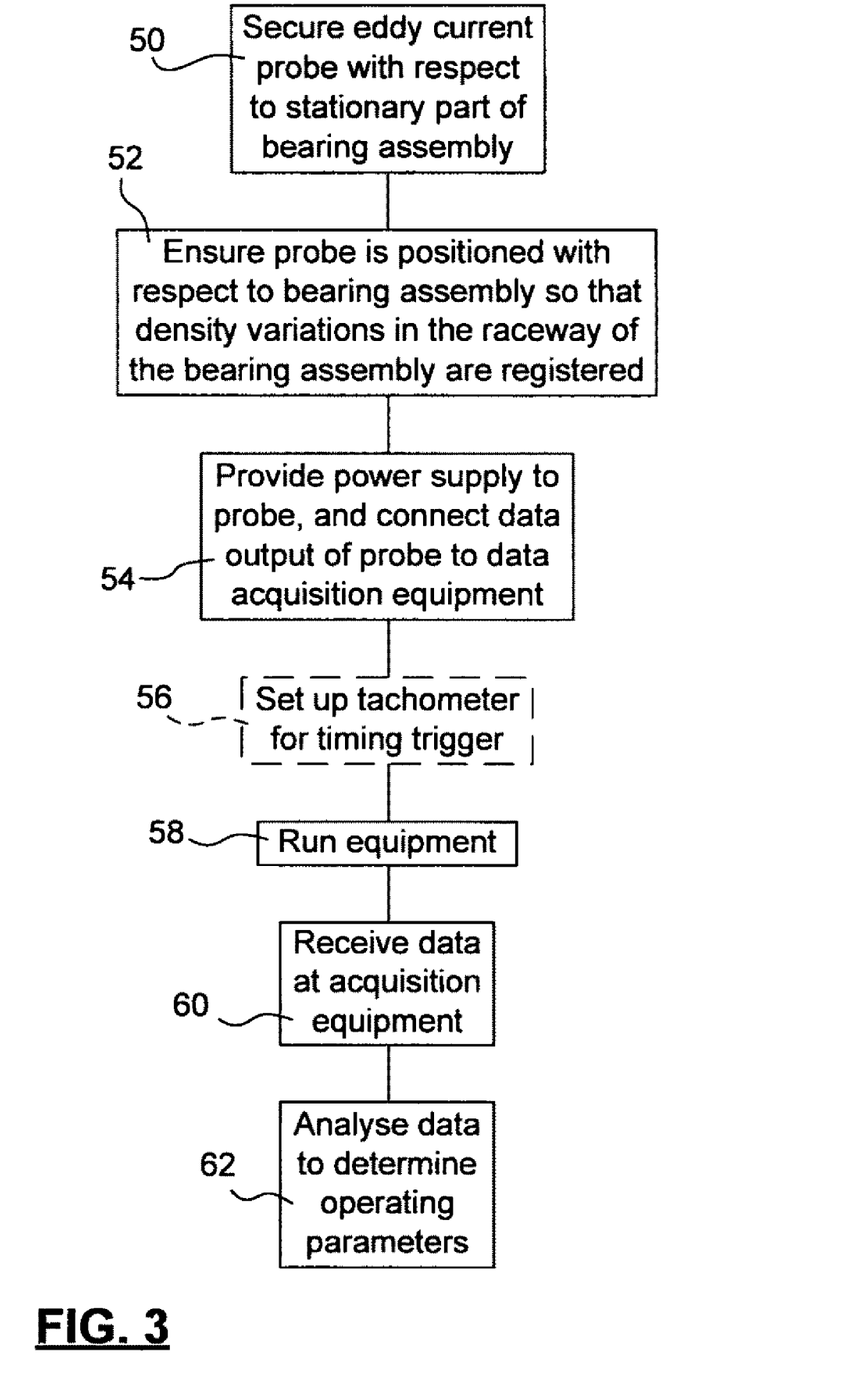
FIG. 3 is a flow chart showing principal steps involved in accordance with a method of the invention.

FIG. 3 is a block diagram illustrating principal steps involved in a process for monitoring operation of a bearing assembly. In step 50, the eddy current probe is secured to the machine or housing adjacent the bearing assembly in such a way that the spatial region of the probe enters the raceway of the bearing assembly at a position intermediate the races. As such the eddy current probe does not detect deflections in a bearing wall of the bearing assembly, but rather detects density changes in the raceway, and does not require passage through any housing that supports the bearing wall.

The eddy current probe can be secured by attaching a fixture on the housing that supports the bearing assembly, on a stationary part of the bearing assembly, or on a part of the machine that is closest to a non-bearing wall of the bearing assembly. It is generally advantageous to isolate the eddy current probe from vibrations to prevent errors in measurements taken by the eddy current probe. The easiest and most economical way of doing this is to secure the eddy current probe as close to the in use position as possible, at a part that is not subject to vibration.

It will be appreciated by those of skill in the art that when applying this invention to existing machines, it may be necessary to provide a path through the machine to the bearing assembly. In one example, a cover of a bearing assembly for bearing principally radial forces, can be provided with a through-bore of a size to accommodate the probe. If the bearing assembly is tested in isolation or a part of a machine is being tested in isolation, the eddy current probe may be coupled directly to a support for the bearing assembly or the part of the machine, which is effectively a part of the machine for the purposes of the present invention.

Once the eddy current probe is attached it is oriented, in step 52, so that the spatial region enters the raceway of the bearing assembly substantially between the races. Power is provided to the probe and the output of the eddy current probe is coupled to data acquisition equipment in any manner known in the art (step 54). A test to verify that the eddy current probe is positioned and oriented adequately may be performed.

As will be appreciated, eddy current probes are designed to operate within established regimes. The rate of pulses and detections may be specified within a range, in some equipment. Selection of a specific eddy current probe is within the purview of the person of skill in the art having regard to the spatial constraints of the bearing assembly, rate of revolution of the bearing assembly, a quality of the signal response, a number, size, and density of bearing elements, a configuration of the bearing assembly, and any constraints regarding signal processing. In general the sampling is performed at a rate that is higher than the cycling rate of the cage, but need not be less than the cage rate divided by the number of bearing elements, if the information from successive cycles is superimposed to produce a higher resolution, and/or higher quality average of the cycles.

Optionally, in step 56, a tachometer or the like may be used to produce a signal indicating a period of the bearing assembly in use. The tachometer may be correlated with the period to provide a correlation of data from successive cycles to provide an effectively higher resolution and/or a higher quality signal representing an average of the successive cycles.

In step 58, the equipment is run so that the bearing assembly is driven. As explained above, this may be operation of the equipment for it's intended deployment, this may involve running the equipment in a test setting, this may involve running a part of a machine in isolation (either as part of the machine as a whole, or removed therefrom) driven by a drive of the machine or driven by an external test driver, for example, or may involve testing the bearing assembly on a test apparatus.

Consequently data is sent to the data acquisition equipment (step 60). The data acquisition equipment may be a general purpose computer, or may be a part of a test and verification workstation, or an on-board diagnostic and monitoring system of the machine.

The data from the probe is preferably presented as a voltage modulated analog stream is preferably converted from analog to digital so that the data may be subjected to analysis by a digital computer. The data may further be filtered to remove noise or smoothed in any known manner, in either the analog or digital formats.

The data may be analyzed (step 62) in the time domain and/or the frequency domain. If the bearing assembly is intended for use within a narrow range of frequencies, i.e. under a substantially constant load, at a fixed speed, with a constant lubrication program, the analysis may simply consist in applying a bandpass filter to the signal, and determining an amplitude of the resulting filtered signal. For example, two or three copies of the signal may be subjected to different bandpass filters having center frequencies at the expected BPF (and a pass band corresponding to an acceptable range of BPF frequencies), and the shaft rate, or the cage rate, respectively. Changes in the mean amplitude, ratio of the amplitudes of the different filtered signals, and/or rates of changes may be indicators of changing conditions of the bearing assembly.

The availability of frequency domain detection software and its efficiency for identifying frequency components from a time domain signal leads the applicant to prefer frequency domain imaging, especially when a complete picture of performance conditions are desirable. An advantage of the frequency domain representation of the signal is that noise is more easily removed, and an intensity and peak frequency of the response is easily identified.

The data may be subjected to a Fast Fourier Transform (FFT), or like transformation to represent the data in a frequency domain. This may be performed by dividing the time domain data into units of time. These units may correspond to respective cycles of the bearing assembly as identified by the tachometer, if one is used. Alternatively, the units may correspond to a statistical number of cycles.

One application of the present invention is a probe with a processor for controlling power supply to the probe, transforming the resistance modulated signal from the probe into a voltage modulated signal, analyzing the voltage modulated signal to identify a frequency having a highest intensity, and outputting the amplitude and the intensity of the identified frequency to a user interface.

This technique may be applied to the health monitoring of bearings where baseline data may be compared to long-term trends. Deviations from the base line could be indicative of changes to bearing operational parameters (oil flow, oil temperature, load, misalignment, etc.), or the formation of a bearing element, cage or raceway defect. Presence or formation of peaks, pulsating or sliding peaks and variations in the time domain signal can all be used to establish a problem or change in the bearing assembly condition. For example, an increase in noise, an increase in a number of frequency components, a change in relative amplitudes of the frequency components, a change in frequency of the peaks, could all be used to indicate changing conditions of the bearing assembly. Although useful information can be extracted from the time domain signal, the FFT is a convenient way to extrapolate the frequency component data. The fundamental train frequency (FTF), and especially the BPF are useful for monitoring purposes and to determine bearing health. The BPF is very sensitive to any change made to the bearing.

Applicant has found that an amplitude of a peak in the neighbourhood of the frequency of revolution of the shaft indicates whether the bearing assembly has been correctly seated in the housing.

Calculations

The Fundamental Train Frequency (FTF) is the cage rotational (angular) speed, given by Eq. 1:

$$FTF = \frac{s}{2}\left(1 - \frac{B_d \cos\phi}{P_d}\right)$$

where: s is a difference in angular velocity (°/s) between the two races, $B_d$ is a maximum diameter of the bearing elements, $\phi$ is an angle between contact points of the bearing elements and the axis of rotation (i.e. 0° in the embodiment of FIGS. 1 and 90° in the embodiment of FIGS. 2), and $P_d$ (bearing pitch) is a diameter of the center path of the raceway through which the nominal centers of the bearing elements pass, i.e.:

$$P_d = \left(\frac{OR + IR}{2}\right),$$

where OR is a diameter of the outer race, and IR is a diameter of the inner race (IR=OR in the axial load bearing assembly). The operator in Eq. 1 is plus if the inner race is stationary and minus if the outer race is stationary. This formula does not apply to thrust bearings (i.e. axial load bearings), in which case the Pd would have to be measured or looked up in the supplier catalogue.

Eq. 1 is the theoretical angular speed (°/s) of the cage under no skidding conditions. The cage frequency $f_c$, in revolutions per minute is calculated by dividing the FTF by 60. The inverse of the cage frequency ($f_c^{-1}$) is the cage period, a length of time it takes for the cage to revolve. Accordingly, under no skid conditions, the ratio between the calculated and actual cage rotational speed will be 1.

Outer and inner race frequencies were calculated using, Eqs. 2, and 3, respectively:

$$BPFO = s\left(\frac{N_b}{2}\right)\left(1 - \frac{B_d \cos\phi}{P_d}\right)$$

$$BPFI = s\left(\frac{N_b}{2}\right)\left(1 + \frac{B_d \cos\phi}{P_d}\right)$$

where $N_b$ is a number of bearing elements.

EXAMPLES

A comparison of the theoretical and measured bearing cage frequency was made based on the equations outlined in the foregoing calculation section. A ratio of the frequencies was calculated to assess the amount of bearing element skidding within the bearing.

Experimental Setup

Figure 4:
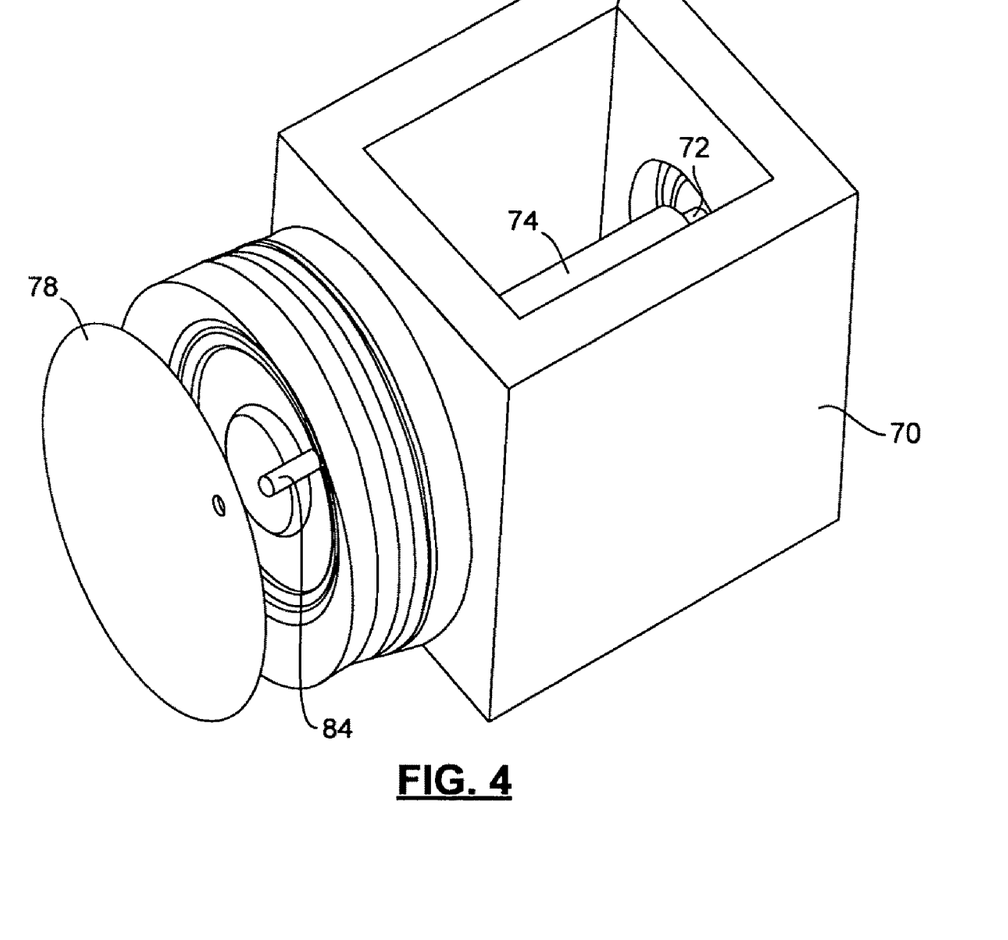
FIG. 4 is a schematic illustration of a test rig used to demonstrate the invention.

A test rig shown in FIG. 4, supported a radial load bearing assembly substantially as shown in FIGS. 1, except that it contained 16 cylindrical bearing elements.

The rig consisted of a hollow support block 70, drive shaft 72 coupled with a support shaft 74, bearing retainer (not in view), a pair of bearing assemblies proximal and distal (not shown), a bearing lubrication system (not shown) and shaft drive assembly (not in shown). The support shaft 74 was supported by a bearing assembly in the support block 70, and the drive shaft 72 was supported at the drive assembly with another bearing assembly (not shown). The drive shaft 72 was driven by a pulley and belt system using a hydraulic motor (not shown).

The tested bearing assembly 80 was housed by the bearing retainer at a proximate end (as shown) opposite to the driven end of the support block 70. The inner race of the test bearing assembly 80 was interference fitted to a steel hub that was also interference fitted to the proximal end of the support shaft 74. The bearing retainer was a steel housing for supporting the outer race of the test bearing.

A cover plate 78 was modified to support a probe 84 and position it axially aligned with a cage area of the bearing assembly 80.

Static loads were applied to the test bearing by a hydraulic ram connected to the outer housing of the bearing through a cable and spring arrangement. A load cell was installed between the hydraulic ram and spring to measure the static load. An optical sensor was located at the drive end of the shaft to measure shaft angular velocity. The bearing assembly was taken from a gas turbine, and was tested under several different radial loads and angular velocities to obtain skid data and to evaluate the applicability of the BPFO measurement method.

The probe 84 was a Bently Nevada 3300 5 mm transducer probe, consisting of a proximitor TM (proximity sensor), and extension cable. A Circuit-Test DC power supply PS-3230 was used to power the proximitor sensor (−17.5 Vdc to −26 Vdc. The output (approx. 0 to −20 Vdc, or 200 mV/mil) of the sensor was then connected to DAS for recording and analyzing. The optical sensor was also connected to the recorder/analyzers as a speed reference. The analyzers were setup to receive scaled voltage input permitting the viewing and recording of the output of the proximitor. The probe was positioned approximately 0.040″ from the bearing elements in the raceway.

Any DAS system that will display the analog signal in either a time domain and/or the frequency domain can be used. In some applications the data may be recorded for off-line processing, inspection and/or analysis. As will be appreciated by those of skill in the art, the raw signal can be post processed using a variety of different programs. Two different DAS systems were used to verify the experiment: a portable, real-time, noise and vibration analyzer (Oros of Dulles Va., model OR25 PC-Pack II—Model 300) and a dynamic data recorder/viewer system (E-DAS analysis software). They both recorded and displayed the output of the proximity senor in a similar fashion.

Table 1 shows a test matrix uses and FIG. 4 shows the results. In all cases the lubricant flow rate was 480 Lbs/h, and .98 gallons per minute of 2380 turbine oil, and the temperature was maintained at 82° C. The speed was set to 10.8, 13.5, or 16.2 kRPM, resulting in measured speeds listed in the table.

The first column lists the load applied by the hydraulic ram, measured by the load cell.

The second column lists the shaft speed as measured by the optical sensor. A difference between the measured shaft speed and that of the peak (times 60) that is associated with the shaft speed (third column) indicates that the peak very likely is a measurement of the shaft speed. A standard deviation of these two values averaged over these examples is less than 0.104%.

The fourth and fifth columns correspond to center frequencies of peaks observed in a frequency domain plot of the data. The peaks correspond to the BPFO and FTF values as evidenced by the fact that their ratio is consistently centered around 16 (the number of bearing elements). In fact the standard deviation of the difference of these values (sixth column) is 1.69%, which goes down to 0.048% if the first value is discarded as an outlier. The average is 16.36 (if you include the first row data), and 15.98 if you exclude the outlier. It is noted that the FTF peak measured for the first row is substantially below a noise floor of the measurement apparatus.

The calculated ratio of shaft speed to cage speed under no skid conditions was 2.1612276. The seventh column of Table 1 shows the ratio of center frequencies of the shaft peak to FTF peak as observed from a frequency plot. The ratio of these two peaks changes depending on a load applied to the bearing assembly and the skidding rate. It is noted that the higher the loading of the bearing assembly, and the higher the shaft speed, the closer the ratio approaches the no skid calculated ratio of shaft to cage speeds.

A ratio of the measured BPFO to a computed no skid BPFO is a measure of how well the movement of the bearing elements corresponds to the prescribed equation. A measure of skidding represented in the last column of Table 1 shows is one minus this ratio as a percent. This is a useful measure for determining how much wear the bearing elements are subjected to, and whether the bearing is functioning within established parameters.

Figure 5:
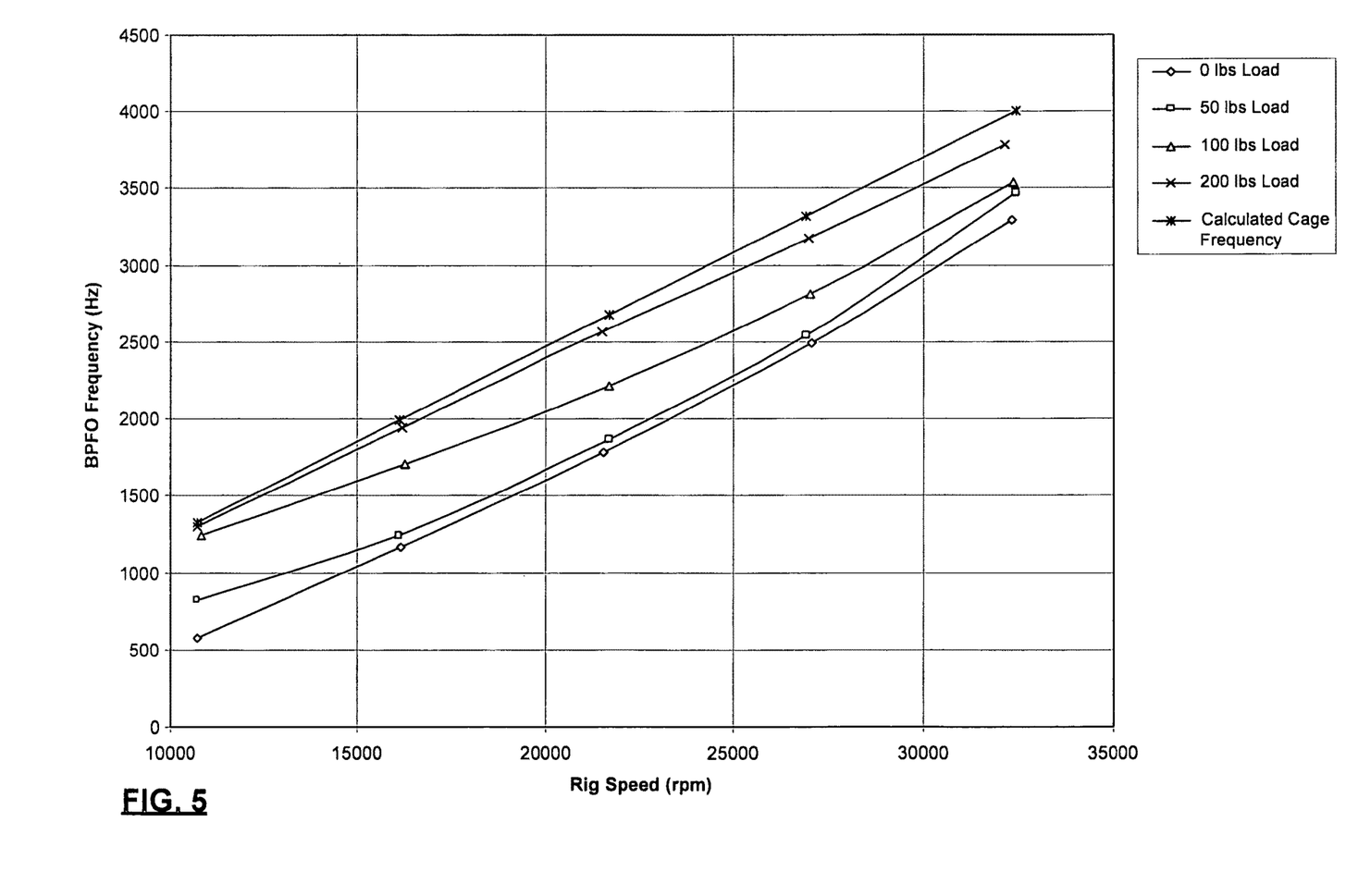
FIG. 5 is a plot of observed BPFO frequency as a function of rig speed for various loads, as well as a theoretical curve for comparison.

FIG. 5 is a plot of BPFO as a function of rig speed for 4 different loads and, for comparison, the Eq. 3 is also plotted. It is noted that with a weighting of 200 lbs the measured BPFO very nearly approximates non-slip operation of the turbine. The measured BPFO conforms nicely with the calculated non-slip operation BPFO according to Eq. 2.

TABLE 1

Test Matrix

| Wt (Lb) | Shaft speed (RPM) | Shaft peak × 60 (RPM) | BPFO peak (Hz) | FTF peak (Hz) | Ratio of BPFO to FTF | Ratio of Shaft peak to FTF | Skidding (%) |
|---|---|---|---|---|---|---|---|
| 0 | 10743 | 10727.4 | 574.62 | 24.4 | 23.55 | 7.327459 | 56.65022 |
| 0 | 16173 | 16159.2 | 1163.94 | 72.72 | 16.00578 | 3.703520 | 41.67271 |
| 0 | 21552 | 21549.6 | 1781.33 | 111.06 | 16.03935 | 3.233928 | 33.0133 |
| 0 | 27040 | 27054 | 2490.23 | 156.2 | 15.94257 | 2.886684 | 25.36122 |
| 0 | 32303 | 32277.6 | 3295.9 | 207.23 | 15.90455 | 2.595956 | 17.30811 |
| 50 | 10733 | 10717.8 | 820.09 | 51.08 | 16.05501 | 3.497063 | 38.07412 |
| 50 | 16143 | 16143.6 | 1238.41 | 77.58 | 15.96301 | 3.468162 | 37.82555 |
| 50 | 21676 | 21667.8 | 1868.79 | 116.43 | 16.05076 | 3.101692 | 30.1264 |
| 50 | 26912 | 26913 | 2539.06 | 159.27 | 15.94136 | 2.816198 | 23.53569 |
| 50 | 32425 | 32446.8 | 3466.8 | 217.09 | 15.96941 | 2.491041 | 13.34761 |
| 100 | 10850 | 10869 | 1243.75 | 77.75 | 15.99678 | 2.329904 | 7.095848 |
| 100 | 16290 | 16263 | 1705.72 | 106.56 | 16.00713 | 2.543637 | 15.13699 |
| 100 | 21676 | 21655.8 | 2210.86 | 138.5 | 15.96289 | 2.605993 | 17.33649 |
| 100 | 27014 | 27046.8 | 2807.62 | 176.53 | 15.90449 | 2.553560 | 15.76721 |
| 100 | 32334 | 32314.8 | 3540.04 | 221.37 | 15.99151 | 2.432940 | 11.26795 |
| 200 | 10733 | 10708.8 | 1299.53 | 81.15 | 16.01393 | 2.199384 | 1.871096 |
| 200 | 16216 | 16198.8 | 1946.04 | 121.8 | 15.97734 | 2.216585 | 2.738762 |
| 200 | 21511 | 21531 | 2563.48 | 159.6 | 16.06191 | 2.248434 | 3.416909 |
| 200 | 26963 | 26976.6 | 3173.83 | 199.33 | 15.92249 | 2.255606 | 4.600254 |
| 200 | 32132 | 32127.6 | 3784.18 | 237 | 15.96700 | 2.259325 | 4.552228 |

Example A

Comparisons of Measurements of Bearing During Testing

Figure 6A:
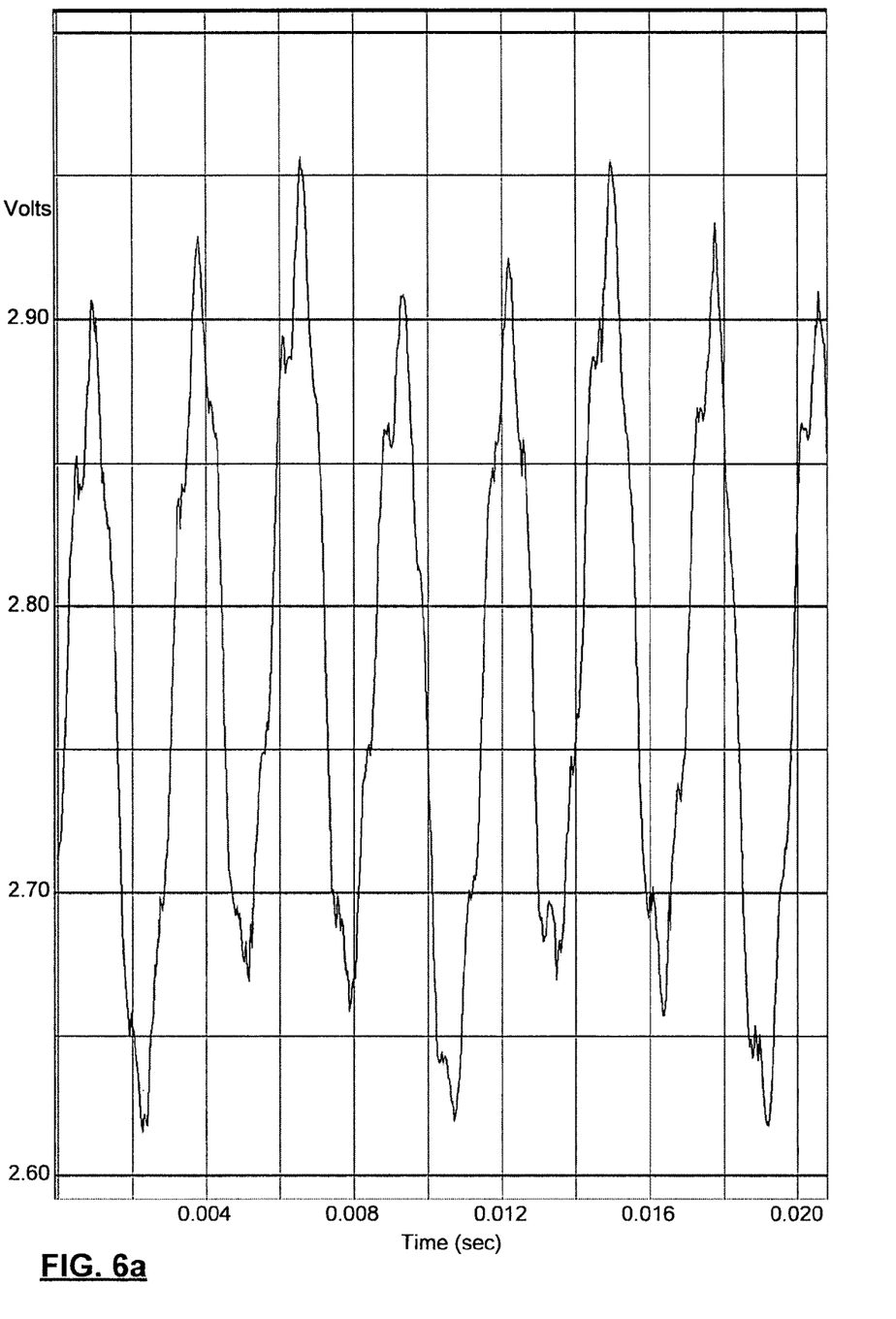
FIGS. 6a b are time and frequency domain signals output of the eddy current probe from a bearing assembly under light operating conditions.
Figure 6B:
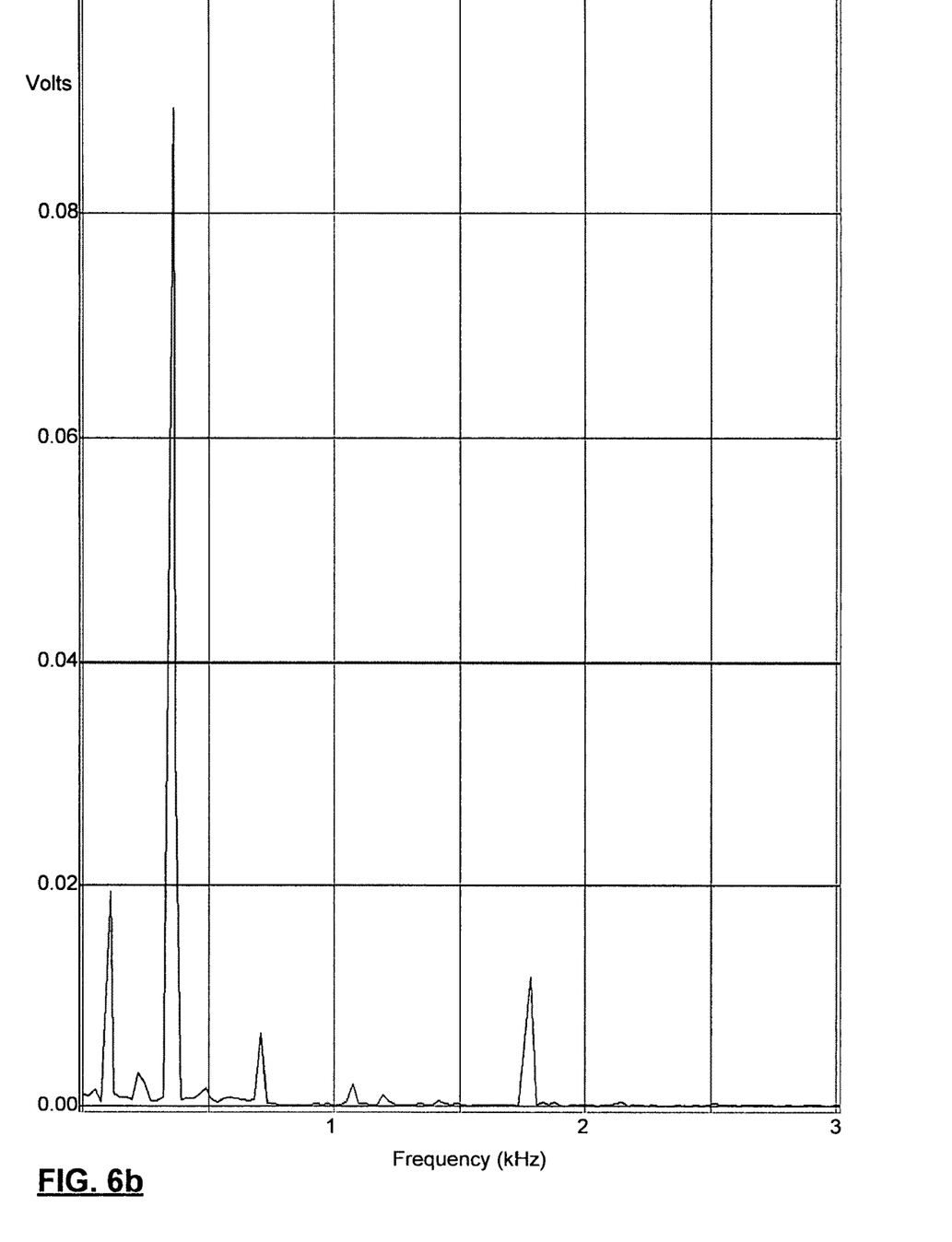

FIGS. 6a,b are graphs of time domain and frequency domain signals produced using the above-described setup using the OR25 analyzer, at the beginning of the test matrix, that is using a new, substantially defect free bearing assembly. The rig is driven under a constant load at a set rate of 21,600 rpm.

In such a signal, three prominent features are expected: those that vary with the frequency of the shaft (i.e. having a frequency corresponding to the difference in angular speeds of the opposite races), those that vary with the cage rate, and those that vary with the bearing elements within the raceway (generally the cage rate time times the number of balls $N_b$, which is 16 in the present example). Naturally there are smaller order harmonic affects expected around these frequencies.

The signal in the time-domain graph shows a principal periodicity at about 0.0028 sec, which corresponds to a frequency of about 360 Hz. This corresponds to a shaft speed, and the amplitude of this peak indicates that the shaft is misaligned. The misalignment of the shaft and inner race was measured to be 1.5 mil. The tolerances of the rig used for testing did not permit a higher precision mounting of the bearing assembly, and thus this artifact is in all of the data. It will be noted that the BPFO can still be readily determined from the signal, and the artifact has only a localized effect in the frequency domain signal shown in FIG. 6b (the strong peak near 360 Hz).

The second highest peak (near 900 Hz) is attributed to the cage. The ratios of the frequencies of the three largest peaks confirm that they correspond to the cage rate, the shaft rotation rate, and the BPFO respectively.

The third highest peak (near 1800 Hz) is a detected ball pass frequency (BPFO as the detector is located on the stationary outer race of the bearing assembly used). The bearing assembly has a calculated no-skid BPFO of 2670 Hz, indicating a much higher skid rate than would normally be desired with the lubrication scheme used. The high skid rate is attributed to a substantially load-free bearing assembly.

Figure 7A:
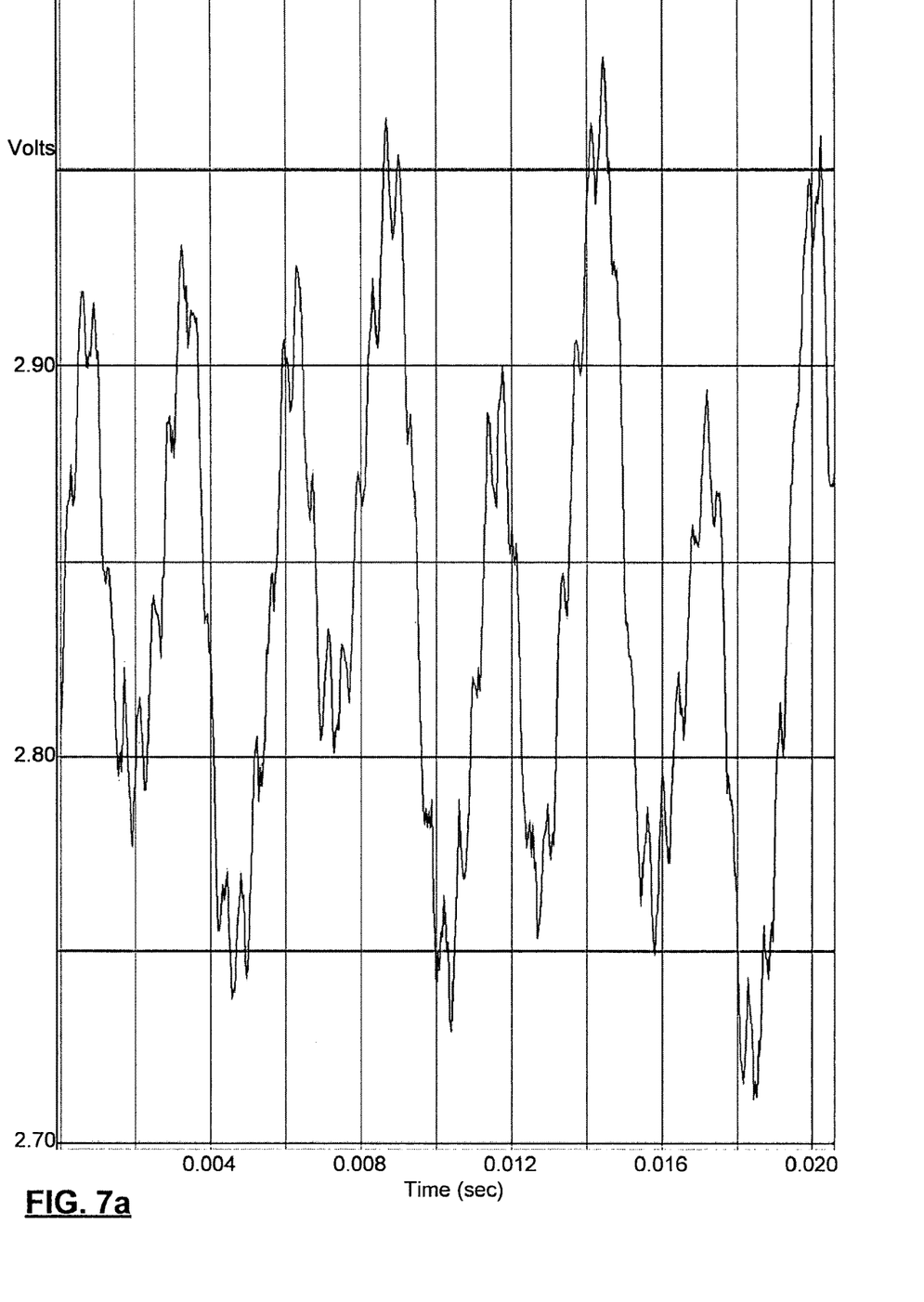
FIGS. 7a b are time and frequency domain signals output of the eddy current probe from a bearing assembly under heavy operating conditions.
Figure 7B:
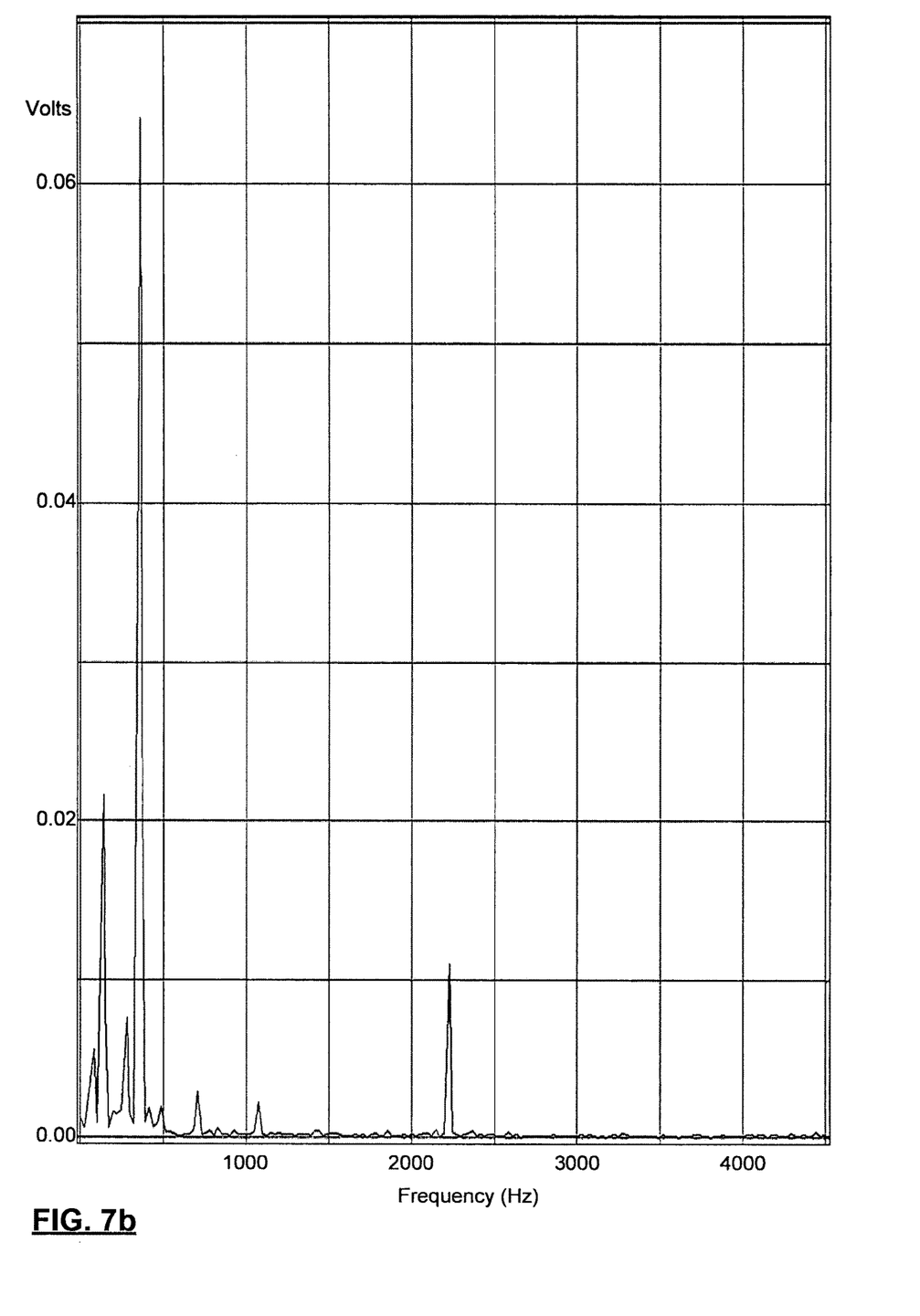

For comparison, FIGS. 7a,b show measurements taken after about 50 hours under difficult operating conditions (varying loads, oil flow, and speeds). As before, FIGS. 7a,b respectively show time domain, and (FFT) frequency domain of a signal. After the heavy operation, the FFT and time domain are much noisier. There are several other peaks in the FFT and the time domain signal develops many more spikes. This indicates that noise may be a useful measure of the operating conditions of a bearing assembly. For example, if the three peaks are removed from the signal, a mean amplitude of the Fourier plot would be a useful measure of the condition of the bearing assembly.

The third highest peak (near 2200 Hz) is a detected ball pass frequency (BPFO as the detector is located on the stationary outer race of the principally radially-bearing assembly used). This corresponds to a calculated no-skid BPFO of 2670 Hz, as before, indicating a skid rate of much closer to a desirable skidding rate for the bearing assembly in operation. As will be appreciated by those of skill in the art, if bearings are worn or pitted, or lubrication is insufficient, the bearings tend to have more traction and accordingly a skidding rate decreases. Accordingly a frequency range about a desired skidding rate may be used to determine whether operation of the bearing assembly is within established parameters.

Example B

Measurement of a Damaged Bearing

Figure 8:
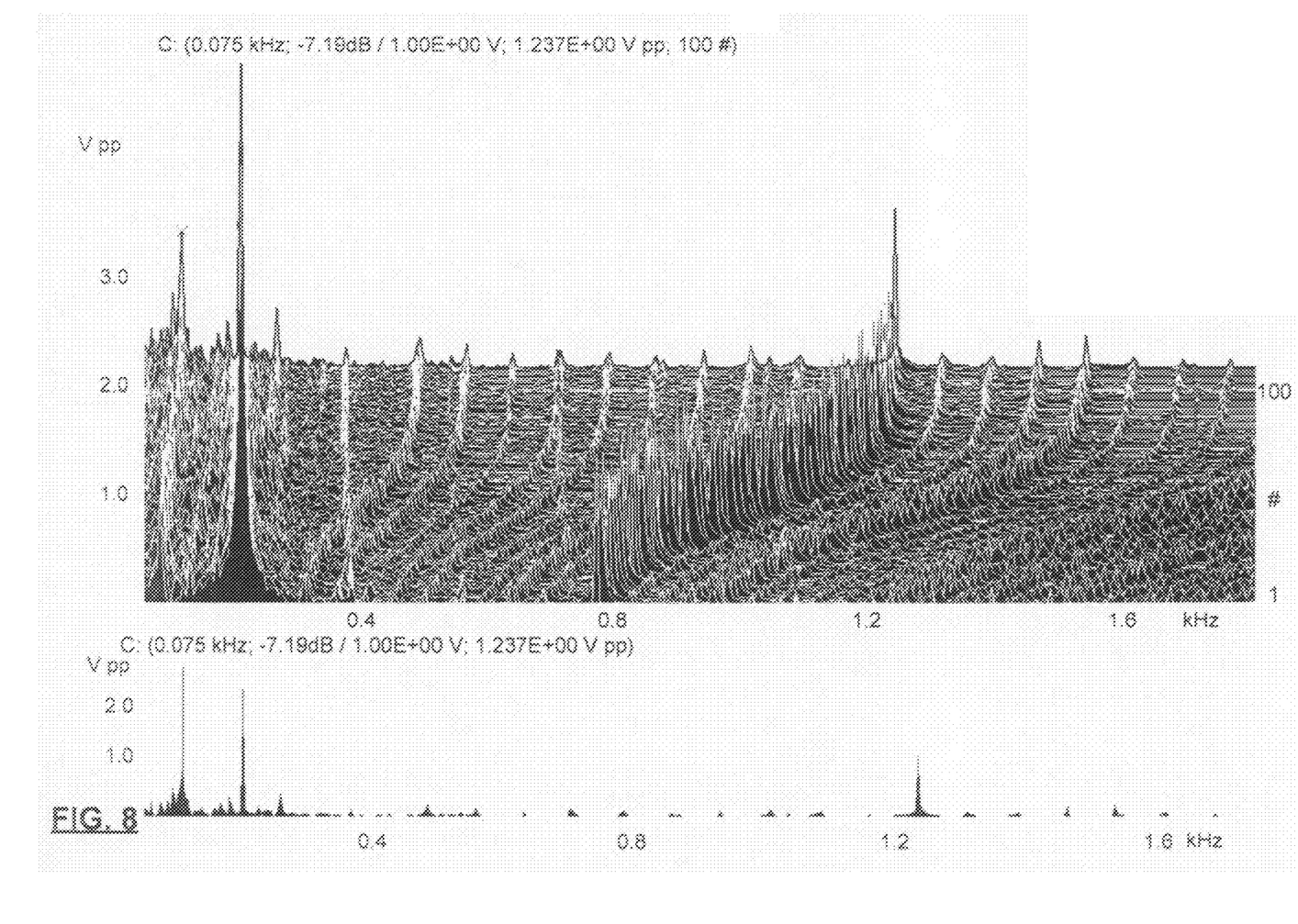
FIG. 8 is a waterfall plot showing output of the eddy current probe from a damaged bearing assembly.

FIG. 8 is a waterfall plot showing fast Fourier transforms (FFTs) of successive 200ms time intervals on successive lines, from a signal captured from a damaged bearing operating under a constant speed with a varying load (0-100lbs). The wandering of the BPFO peak (initially .75 kHz 1.22 kHz) is indicative of the stress change from 0-100 lbs, and is normal. Misalignment of the bearing (0.0015" in) is again presented by the amplitude of the shaft rate peak at around 180 Hz observed from the shifting of the outer race ball pass frequency (BPFO) under varying load. It will be noted that some of the peaks near the shaft speed are substantially invariant throughout the change in load, but that many harmonics of the BPFO and cage frequency are produced. This suggests that damaged bearings can be detected by looking at a number and amplitude of peaks substantially corresponding to integer multiples of the cage frequency.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. An apparatus for monitoring operation of a bearing assembly, the apparatus comprising:
   an eddy current probe for detecting a change in material density within a spatial region in front of a tip of the probe; and
   a fixture mounting the probe in a stable position with the tip of the probe proximate a raceway of the bearing assembly so that part of the spatial region enters the raceway at a position intermediate opposing races that provide supporting walls of the raceway, whereby the probe is not directed substantially through either supporting wall.

2. The apparatus of claim 1 wherein the fixture is mounted on or adjacent a relatively stationary part of the bearing assembly.

3. The apparatus of claim 1 wherein the bearing assembly is for bearing a principally radial load, and the probe is positioned with the tip substantially intermediate an inner and an outer race above or below the raceway, the probe being directed at least partially in a direction of an axis of rotation of the bearing assembly.

4. The apparatus of claim 3 wherein the probe is directed at least mostly in the direction of the axis of rotation.

5. The apparatus of claim 1 wherein the bearing assembly is for bearing a principally axial load and the probe is positioned with its tip intermediate the races of the raceway, the probe being directed at least partially in a direction radially inwardly or outwardly of an axis of the bearing assembly.

6. The apparatus of claim 5 wherein the probe is directed at least mostly in the radially inwardly or outwardly direction.

7. A bearing assembly with a condition monitor, comprising:
   the apparatus of claim 1; and
   the bearing assembly comprising a rotating part having a meeting surface defining a first of the races, a supporting part having a complementary surface defining a second of the races, and a plurality of bearing elements, the rotating and supporting parts arranged so that the first and second races face each other to define the raceway for the bearing elements.

8. The bearing assembly of claim 7 wherein the fixture is mounted on or adjacent the stationary part of the bearing assembly.

9. The bearing assembly of claim 7 wherein the bearing assembly is for bearing a principally radial load and the probe is positioned with its tip substantially intermediate the inner and outer race axially above or below the raceway, the probe being directed at least partially in a direction of an axis of rotation of the bearing assembly.

10. The apparatus of claim 8 wherein the probe is directed at least mostly in the direction of the axis of rotation.

11. The bearing assembly of claim 7 wherein the bearing assembly is for bearing a principally axial load, and the probe is positioned with its tip intermediate the inner and outer race, the probe being directed at least partially in a direction radially inwardly or outwardly of the bearing assembly.

12. The apparatus of claim 11 wherein the probe is directed at least mostly in the direction of the axis of rotation.

13. A method for producing an apparatus for monitoring operation of a bearing assembly, the method comprising:
   providing an eddy current probe for detecting a change in material density within a spatial region in front of a tip of the probe; and
   retaining the probe in a stable position relative to a stationary part of the bearing assembly to position the tip of the probe with at least part of the spatial region crossing a raceway of the bearing assembly at a position intermediate inner and outer races that provide supporting walls of the raceway, whereby the probe is not directed substantially through either supporting walls;
   whereby supplying power to the probe and driving the bearing assembly permits detection of bearing elements circuiting the raceway.

14. A method for monitoring operation of a bearing assembly, the method comprising:
   providing an eddy current probe for detecting a change in material density within a spatial region in front of a tip of the probe;
   retaining the probe in a stable position relative to a stationary part of the bearing assembly to position the tip of the probe with at least part of the spatial region passing into a raceway of the bearing assembly from a position intermediate inner and outer races of the raceway that provide supporting walls of the raceway, whereby the probe is not directed substantially through either supporting walls;
   supplying power to the probe from a power supply to activate the probe to detect changes in material density within the raceway at a given sample rate while the bearing assembly is in operation;
   capturing data from the probe in a stream of data at a sample rate greater than a cycling rate of a cage of the bearing assembly; and
   analyzing the captured data to determine properties of the bearing assembly in use.

15. The method of claim 14 wherein analyzing further comprises determining a ball pass frequency of the bearing assembly.

16. The method of claim 14 wherein analyzing comprises identifying noise and signal patterns within a time domain signal.

17. The method of claim 14 wherein analyzing comprises applying a Fourier transform to the data to identify peak detected frequencies corresponding to a shaft speed, a cage speed and a ball pass frequency.

18. The method of claim 14 wherein analyzing comprises identifying at least one of: an increase in noise, an increase in number of peaks, a change in relative amplitudes of the peaks, and a change in frequency of the peaks, with respect to one of: a baseline healthy measurement, a previously established operating regime, and a previous measurement interval.

19. A kit for monitoring operation of a bearing assembly, the kit comprising:
   an eddy current probe for detecting a change in material density within a volume in front of a tip of the probe; and
   instructions for effecting the method of claim 13.

20. The kit of claim 18 further comprising program instructions for carrying out an analysis of data captured from the eddy current probe to determine properties of the bearing assembly in use.

* * * * *